United States Patent [19]

Winters et al.

[11] Patent Number: 4,629,451
[45] Date of Patent: Dec. 16, 1986

[54] STEREOTAXIC ARRAY PLUG

[75] Inventors: Arthur Winters, Short Hills; Casper S. Molee, Bloomfield, both of N.J.

[73] Assignee: Victory Engineering Corp., Springfield, N.J.

[21] Appl. No.: 779,170

[22] Filed: Sep. 23, 1985

[51] Int. Cl.⁴ .......................... A61M 5/32; A61B 17/36
[52] U.S. Cl. ................................ 604/175; 128/303 B
[58] Field of Search ............... 128/303 B, 303 R, 1 R; 604/175, 264, 49

[56] References Cited

U.S. PATENT DOCUMENTS

| | | | |
|---|---|---|---|
| 3,016,899 | 1/1962 | Stenvall | 604/175 |
| 3,055,370 | 9/1962 | McKinney et al. | 128/303 B |
| 3,298,372 | 1/1967 | Feinberg | 604/8 |
| 4,186,728 | 2/1980 | Van Lontringen | 128/1 R |

Primary Examiner—Richard E. Gluck
Attorney, Agent, or Firm—Albert F. Kronman

[57] ABSTRACT

There is disclosed a surgical stereotaxic array plug of biocompatible material having an outer periphery adapted to be secured in a complementary threaded opening provided in the skull with bores traversing the plug for receiving and positioning therapeutic apparatus and fluid dispensing devices.

11 Claims, 14 Drawing Figures

STEREOTAXIC ARRAY PLUG

FIELD OF THE INVENTION

This invention relates generally to means and a process for reaching selected discrete areas of the brain in order to treat these areas. More specifically, the invention is concerned with improved insert means for effecting microwave hyperthermia of brain tumors, said means being a biocompatible array plug of mechanically and chemically stable material.

PRIOR DISCLOSURE STATEMENT

In the course of surgical and other invasive treatment of the brain, it is common practice to insert numerous needles, probes and/or catheters into the brain and the area to be treated and surrounding tissues. Heretofore, surgeons have found it difficult to accurately insert and leave in position for successive treatment these invasive devices.

OBJECTS AND SUMMARY OF THE INVENTION

An object of this invention is to provide cranium insertable means for receiving and supporting surgical and therapeutic devices.

A further object is to provide a removable mechanical array plug threadable into the cranium and containing a plurality of bores for the insertion and support of invasive devices of the type above-mentioned.

Another object is to provide a plug which is machineable to high accuracy and biocompatible with the patient's tissue so that it may be left in place for extended periods of time.

Other non-elementary objects of the invention are to:
(a) provide a plug with a variety of bore diameters to accommodate catheters, needles, probes, laser modules and the like for treating a human or animal brain;
(b) provide a plug which can be sutured in place;
(c) provide a plug which can be positioned through the use of a spanner wrench;
(d) provide a plug with radiopaque top markings for X-Ray identification and location of an area undergoing treatment.

Additional objects of this invention are to provide an array plug which is relatively inexpensive to manufacture, readily sterilizable, sturdy in construction, reliable and efficient in use.

A still further object of this invention is to provide the physician with a tool and method to overcome previous problems of placement and support during microwave hyperthermia treatment.

The material selected for the plug is accurately machineable, compatible with bone tissue matter, and can be sterilized without losing its mechanical characteristics.

The insert array plug of the invention allows the physician to maintain probes at discrete distances apart, allows for precise placement of interstitial needles, microwave probes and temperature measuring catheters. It has the added feature of being able to be sutured to the skull and contains radio opaque markers for X-Ray identification and location.

BRIEF DESCRIPTON OF THE DRAWINGS

The present invention will be better understood by referring to the accompanying drawings whose figures show in non-limiting fashion various forms thereof, and wherein.

SUMMARY OF THE INVENTION

Figure 1:
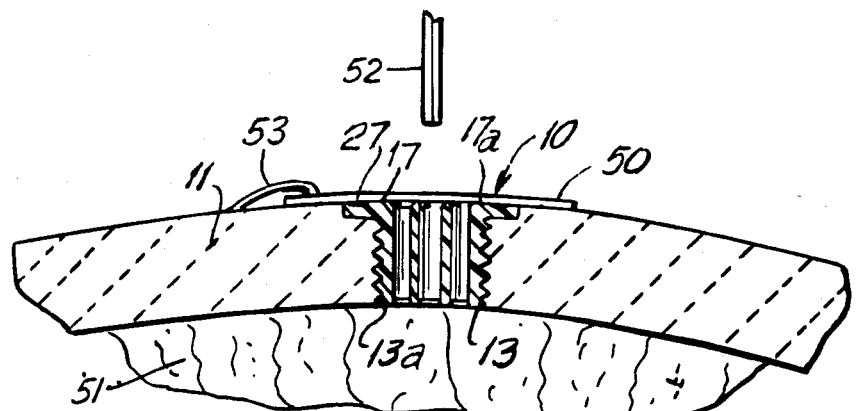
FIG. 1 is a cross-sectional view of the plug of the invention inserted in a partially shown cranium.

Referring descriptively to the drawings, FIG. 1 shows generally the apparatus aspect of this invention. As shown, a generally cylindrical array plug 10 made of biocompatible plastic or other material inert to bodily activities in the area of operation is fitted in area 11 of the scalp. Suitably, halogenated polymers such as "Teflon" and "Delrin" are used to make the plug. The area 11 is the preshaven scalp area. An opening 13 with threaded walls 13a is bored to threadably receive the plug diameter, into the pericranium. The plug is screwed into opening 13 using a spanner wrench 31 which fits in cannula openings 40, 42, 46, 48 (FIG. 14) or other means until the plug's top surface 17 is flush with the skull surface or alternately recessed therein.

The top 17 of the plug has radial markings 17a formed of suitable radiopaque material. These markings serve to locate the orientation of the plug relative to the brain for future reference when X-Rays are periodically taken to determine whether any change has occured in the treated area of the brain 51. Preferably, these markings are reticular lines extending from the outer periphery of the plug to satellite through holes therein.

In its method aspect, the invention resides in the steps of boring and optionally internally threading an opening in the skull above the area to be treated, inserting a complimentary externally threaded stereotaxic plug having an array and bores therein in said opening until the upper surface of said plug is substantially flush with the said skull surface, introducing probe means through said plug bores to administer a required treatment to a selected area of said brain, removing said probe means 52 from said plug and closing or covering said area to be treated.

DISCLOSURE OF BEST MODE OF THE INVENTION

Figure 2:
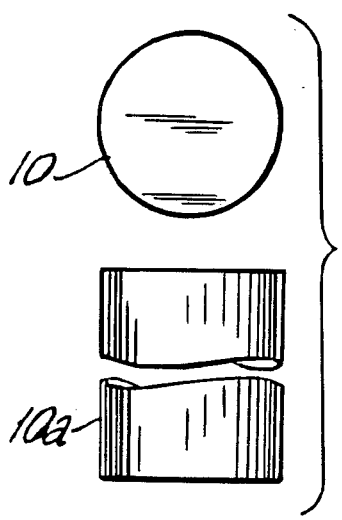
FIGS. 2-13 illustrate successive stages in the fabrication of the plug of the invention.
Figure 3:
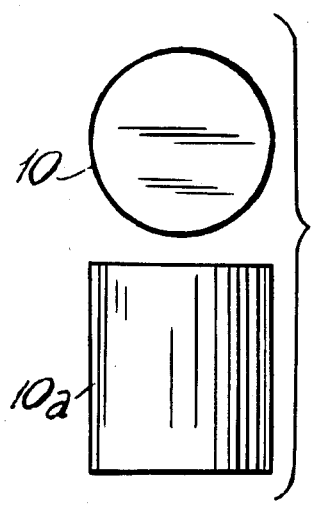

Typical manufacture of a practical array plug insert in accordance with this invention is accomplished by the following steps where actual dimensions are given by way of example only:

1. Utilizing ⅝ inch "Delrin" or "Teflon" round stock (FIG. 2), 1.0 inch (deep) sections (FIG. 3) are cutoff from the stock.

Figure 4:
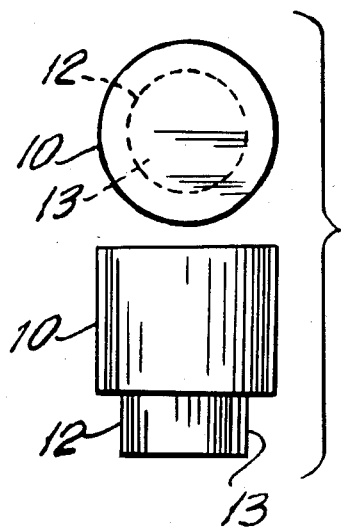

2. Machine one end 12 to an O.D. of 15 mm to a depth of 7.0 mm (FIG. 4).

Figure 5:
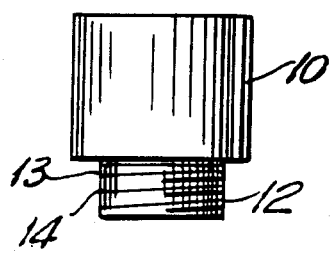

3. Into the 15 mm×7.0 mm diminished section 13, cut a thread 14 that is of the order of 16 threads per inch to a depth of 6.8 mm (FIG. 5).

Figure 6:
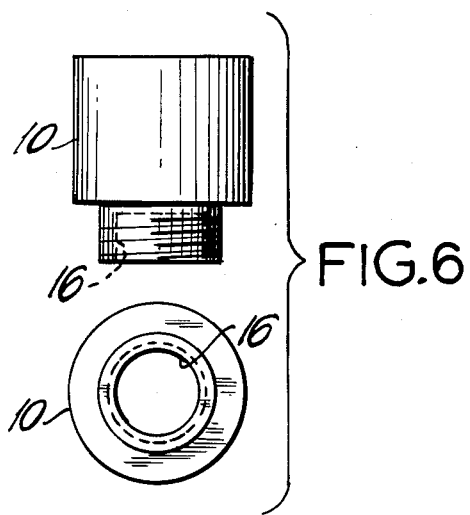

4. Mill out center 16 of threaded section to a depth of 6.0 mm so that the resulting O.D. is 15 mm and the I.D. is 13.5 mm (this is a 1.5 mm rim thickness) (FIG. 6).

Figure 7:
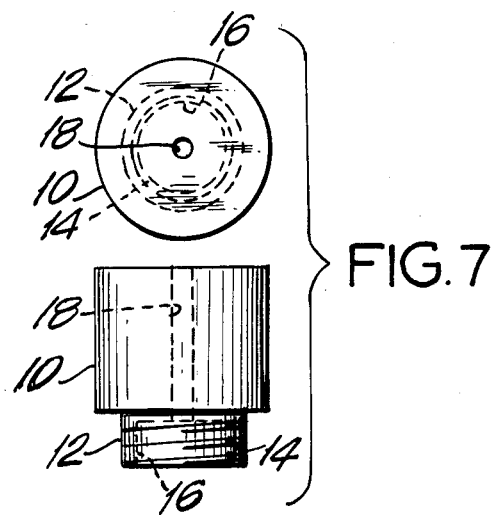

5. Locate center point of plug and drill a central through hole 18 which is 2.9 mm in diameter (FIG. 7).

Figure 8:
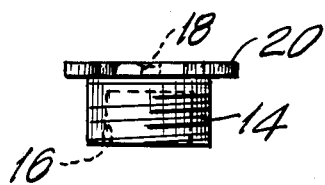

6. Face off the top portion such that the overall length of the plug is 9.5 mm and the head 20 is 1.5 mm (FIG. 8).

Figure 9:
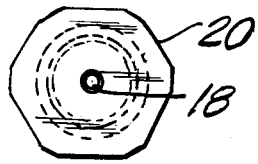

7. Place into a holding fixture and mill top of head 20 to give it a noncircular shape such as a 120° hexagon (FIG. 9).

Figure 10:
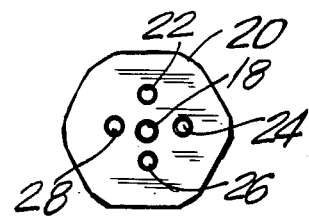

8. As shown in FIG. 10, locate and drill four satellite through holes 22, 24, 26, 28. The location of the holes 22–28 is 4.8 mm center to center from the central hole 18. Each of the four through holes is 2.3 mm in diameter.

Figure 11:
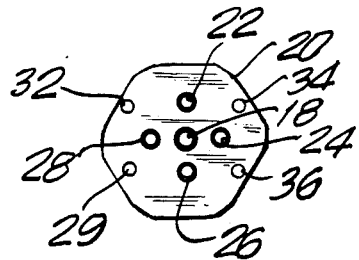

9. Locate and drill four sutures 53 through holes 29, 32, 34, 36 on the outer periphery of plug 10. Their location can be 8.2 mm center to center from central hole. Each of the holes can be 1.0 mm in diameter (FIG. 11).

Figure 12:
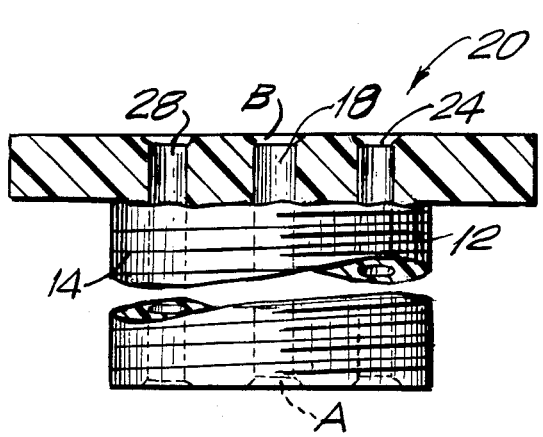

10. Countersink central hole 18 and the four satellite holes 22, 24, 26, 28 on both faces A and B in FIG. 12 to a depth of 0.004 inches (FIG. 12) and the four suture holes 29, 32, 34, 36, on both faces to a depth of 0.002 inches. This will insure easy insertion of needles, probes, etc.

11. Debur all sharp edges, paying special attention to the threaded area 14.

12. Degrease array plug insert 10 in the vapor phase by using "Freon" to remove all residues of oil, grease and miscellaneous materials. Dry the degreased device for three hours at 100° C. to insure no moisture entrapment.

Figure 13:
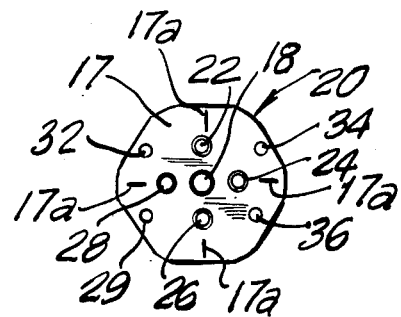

13. Using a fritless, gold or any other suitable radiopaque material such as tantalum powder (type 258) mixed with silicone adhesive to form a paste, deposit or paint a 4.75 mm by 0.8 mm pattern on the top surface 17 in an array fashion 17a (FIG. 13). A stencil is placed on the top of the plug to prevent the material from entering the through bores.

14. Bake the deposited material (in air) at 125° C. for 16 hours.

USE OF THE ARRAY PLUG INSERT OF THE INVENTION IN SURGERY

1. Using suitable equipment, either gas or flash methods, sterilize the plug.

2. Brain area is identified on preshaven scalp area 11 by X-Ray, NMR or CAP (computerized automated psychophysiological scan); scalp is opened and a retractor is used to maintain opening. Pericranium is then opened and retracted and a hole is bored in the skull which is the same size as plug diameter (15.0 mm) which is complementarily threaded with the threads on the plug.

3. The area is then bored in the skull which is the same size as plug diameter (15.0 mm).

4. Using an X-Ray, Cat Scan or NMR (Nuclear Magnetic Resonance) to monitor, radiopaque shunts (not shown) are inserted into appropriate satellite hole locations 20, 22, 24, 26 and then a multipurpose catheter (containing a microwave probe); such as that disclosed and claimed in coassigned copending application, Ser. No. 779,285 filed Sept. 23, 1985 even day herewith; is inserted into the central hole for hyperthermia reaction.

A biopsy needle can be used initially through the central hole for removal and examination of suspect material.

5. After completion of the operation, all shunts, probes, catheters are removed and the plug may, or may not, be left in place by suturing the pericranium utilizing four (4), 1.0 mm suture holes 29, 32, 34, 36.

6. As shown in FIG. 1, the skin flap 50 is then repositioned over the top of plug 10 and sutured. Where the plug is very small, a waterproof adhesive layer can be removably placed thereon.

7. In later uses of plug 10, the skin flap 50 is opened since the plug is accessible for additional insertions. The plug can remain in place for one to six months.

Figure 14:
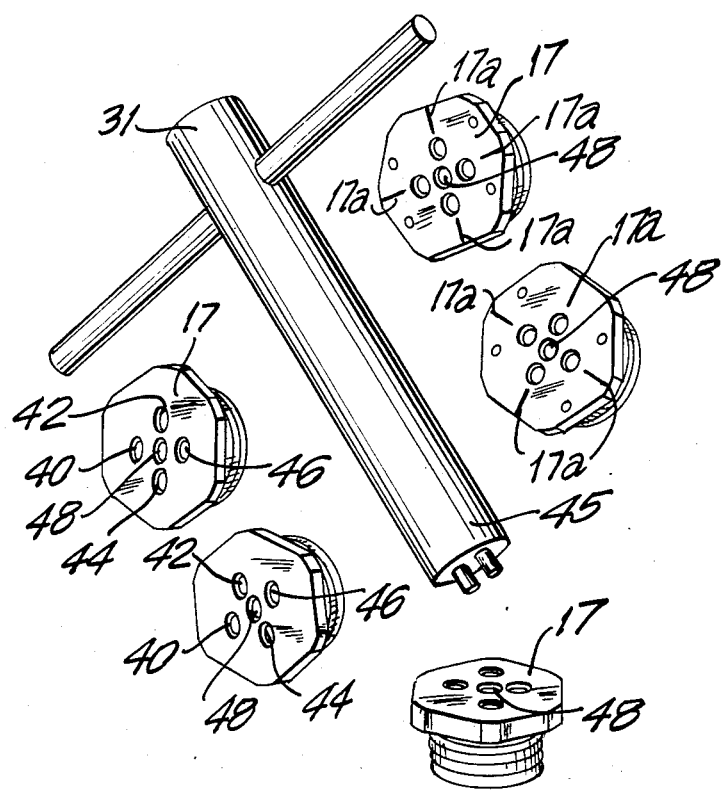
FIG. 14 is a perspective view of a special spanner wrench for screwing in the plug of the invention and of a plug with five cannula openings serving as guides for the implant and for the insertion of probes.

In FIG. 14 the array plug as shown has four cannula openings 40, 42, 44, 46 and central opening 48 which are 5.0 mm apart and serve as guides for an implant or for inserting probes.

In the event the material of the plug were sufficiently hard to be self-threading, the opening in the skull need not be threaded when it is made.

Having thus described the invention, what is desired to be claimed by Letters Patent is:

1. A stereotaxic array plug adapted for threading into a threaded opening made in a skull comprising:
   a shaped body formed of a biocompatible material; said body having a top section; a bottom section a central opening extending therethrough for introducing devices for treating the brain;
   a plurality of satellite through openings about said central opening;
   radiopaque markings on said top section of said body, but not obliterating said openings; and
   threads in said bottom section for screwing into said opening in the skull.

2. The array plug of claim 1, wherein said central opening and said satellite openings are countersunk at least on the upper extremities thereof.

3. The array plug of claim 1, wherein said bottom section has a smaller diameter than said top and has said threads thereon.

4. The array plug of claim 1 further having a plurality of spaced suture openings about said satellite openings.

5. The plug of claim 1, wherein said markings extend from the outer periphery of said top section toward satellite through openings.

6. The plug of claim 1 wherein said markings consist of gold baked thereon.

7. The plug of claim 1, wherein said markings consist of baked tantalum.

8. Brain treating method comprising boring an opening in the skull above the area to be treated; inserting therein a plug comprising a shaped body formed of a biocompatible material; said body having a top section, a bottom section through opening extending therethrough for introducing devices for treating the brain; a plurality of satellite through openings about said central opening; radiopaque markings on said top section of said body, but not obliterating said openings; and threads in said bottom section for screwing into said opening in the skull; until the upper surface of said plug is substantially flush with the upper part of said opening in said skull; introducing probe means through said plug to administer a required treatment to said brain; removing said probe means from said brain and plug and closing the area over said opening.

9. The method of claim 8, wherein a skin flap is made of the scalp to overly the plug, said plug being left in said opening after said treatment.

10. The method of claim 9 wherein said flap is sutured over said plug after treatment of said brain.

11. In combination with a plug as defined in claim 1, a spanning means having pins projecting from the lower portion thereof and adopted to fit in at least two of said openings in said plug for inserting and tightening said plug in an opening made in a skull.

* * * * *